United States Patent [19]

Kudo et al.

[11] Patent Number: 4,699,851
[45] Date of Patent: Oct. 13, 1987

[54] SOLID ELECTROLYTE

[75] Inventors: Tetsuichi Kudo, Setagaya; Go Kawamura, Musashino; Akira Ishikawa, Kokubunji, all of Japan

[73] Assignee: Hitachi, Ltd., Tokyo, Japan

[21] Appl. No.: 910,224

[22] PCT Filed: Jan. 16, 1986

[86] PCT No.: PCT/JP86/00016
§ 371 Date: Aug. 25, 1986
§ 102(e) Date: Aug. 25, 1986

[87] PCT Pub. No.: WO86/04320
PCT Pub. Date: Jul. 31, 1986

[30] Foreign Application Priority Data

Jan. 25, 1985 [JP] Japan ................................ 60-10840

[51] Int. Cl.[4] .............................................. H01M 8/10
[52] U.S. Cl. ....................................... 429/33; 429/191
[58] Field of Search ................... 429/33, 30, 191, 193; 252/62.2

[56] References Cited

FOREIGN PATENT DOCUMENTS 0050536 4/1977 Japan .................................. 429/191

Primary Examiner—Anthony Skapars
Attorney, Agent, or Firm—Antonelli, Terry & Wands

[57] ABSTRACT

The present invention relates to a solid electrolyte comprising a heteropolyacid, the principal component of which is a heteropolytungstic acid and/or heteropolymolybdic acid containing carbon as a hetero atom.

This heteropolyacid is stable and can be easily molded and its preparation is simple.

3 Claims, 1 Drawing Figure

SOLID ELECTROLYTE

TECHNICAL FIELD

The present invention relates to a hydrogen ion (generally its hydrate)-conductive solid electrolyte. Particularly, it relates to a solid electrolyte which is suitably used in electrochemical equipment such as hydrogen-oxygen fuel cell, hydrogen sensor or pH sensor.

BACKGROUND ART

It has been reported by, for example, O. Nakamura et al. in Materials Research Bulletin 17, 231 (1982) that a heteropoly-acid (solid) such as dodecatungstophosphate ($H_3PW_{12}O_{40} \cdot nH_2O$) is a proton-conductive solid electrolyte. However, no heteropolyacids containing carbon as a heteroatom have been known as yet.

DISCLOSURE OF INVENTION

An object of the present invention is to provide a novel solid electrolyte which is suitably used in fuel cells, various sensors, electrochromic display elements or the like.

It has been found that the heteropolyacid containing carbon as a heteroatom to be used in the present invention exhibits a remarkable proton conductivity, that is, it is a proton-conductive solid electrolyte. The heteropolyacid has advantages in that its preparation is simple and that it can be molded more easily than other heteropolyacids. Further, the heteropolyacid is still advantageous in that a firm thin film can be produced from an aqueous solution thereof.

A heteropolyacid solid electrolyte is a solid comprising a heteropolyanion represented by the general formula, $M'_xM_yO_z^{m-}$, and a hydrated proton represented by the general formula, $H(m' H_2O)^+$, wherein proton is conducted. M is generally tungsten(W) or molybdenum(Mo) and P, Si, As and the like are known as the heteroatom M'. The solid electrolyte according to the present invention is represented by the above formula wherein M' is carbon (C) and is a novel electrolyte which has not been known up to this time. Further, though the heteropolyacids of the prior art have been prepared by liquid phase reaction between polytungstic acid (or polymolybdic acid) and an acid containing a heteroatom (for example, dodeca acid), the solid electrolyte of the present invention is prepared by the reaction between tungsten carbide and a solution of hydrogen peroxide.

The heteropolyacid of the present invention is a solid heteropolyacid containing carbon as a heteroatom which comprises a heteropolyanion represented by the general formula, $M'_xM_yO_z^{m-}$ (wherein the ratio of x to y is between 1:12 and 4:12) and a hydrated proton represented by the formula, $H(m' H_2O)^+$. In the above general formula, M' is C and M is at least one element selected from the group consisting of W and Mo. Further, the above formula can be also represented by the formula: $WO_3 \cdot aCO_2 \cdot bH_2O_2 \cdot cH_2O$ (wherein $0.083 \leq a \leq 0.25$, $0.05 \leq b \leq 1$ and $0.16 \leq c \leq 4$).

BEST MODE FOR CARRYING OUT THE INVENTION

Figure 1:
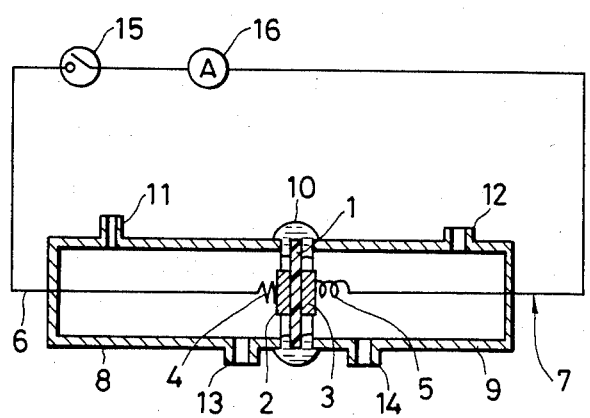
FIG. 1 shows a cross-sectional view of a cell produced by using a solid electrolyte of the present invention.

Examples of the present invention will now be described.

EXAMPLE 1

100 ml of a 15% aqueous solution of hydrogen peroxide ($H_2O_2$) was added to 16 g of tungsten carbide (WC) powder. When gas evolution was reduced, an additional 5 ml of 3% $H_2O_2$ was further added. This procedure was repeated 5 times. The resulting mixture was allowed to stand at a room temperature for 24 hours or over to dissolve the WC, thus obtaining a pale yellow strongly acid solution. This solution was filtered to remove sooty carbon. The excess $H_2O_2$ contained in the solution was removed by decomposition with a platinum gauze having adherent platinum black. The obtained solid electrolyte stock solution was placed in a flat-bottomed glass vessel, heated until just before its solidification and allowed to stand at a room temperature. By allowing to stand for 24 hours or over, a glassy plate was obtained. This solid did not exhibit any X-ray diffraction pattern, that is, it was amorphous. Further, the solid had a molar ratio of C to W of about 1:12. When the solid was heated, it first lost moisture and was decomposed with release of $CO_2$ at about 300° C. into $WO_3$. Infrared or Raman spectroscopic analysis of the solid showed the presence of a strong band of about 950 to 1000 cm$^{-1}$ Further, the infrared spectroscopic analysis thereof showed the presence of an absorption of about 1300 to 1400 which was inherent in the substance. $^{13}C$- NMR spectroscopic analysis of the above solid electrolyte stock solution showed the presence of a resonance absorption at about 167 ppm. It is apparent from the above results that the obtained solid is a kind of heteropolyacids containing carbon as a heteroatom.

A cell shown in FIG. 1 was produced by the use of the above solid plate. In this figure, numeral 1 refers to the above solid plate. Platinum springs 4 and 5 press platinum electrodes 2 and 3 against the both surfaces of the solid plate 1, respectively. The other ends of the springs 4 and 5 are taken out as electric leads 6 and 7. Glass tubes 8 and 9 are bonded to the solid electrolyte 1 with an epoxy adhesive 10. Steam-saturated hydrogen was fed at 10° C. via inlets 11 and 12 and discharged via outlets 13 and 14, respectively. The electromotive force generated between the electric leads 6 and 7 in this step was 0 V. Then, steam-saturated hydrogen was fed via the inlet 11 at 10° C., while a gaseous mixture comprising 10% of steam-saturated hydrogen and 90% of argon was fed via the inlet 12 at 10° C. When the temperature of the cell was 20° C., an electromotive force of 29.1 mV was generated between the lead 6 and the lead 7. The hydrogen concentration of the gas to be fed via the inlet 12 was varied and the electromotive force between the leads 6 and 7 was measured at each of the concentration. The electromotive force E(mV) was varied depending upon the equation:

$$E = 29.1 \log_{10} P_{H_2} \qquad (1)$$

wherein $P_{H_2}$ is hydrogen concentration of the gas fed via the inlet 12.

When oxygen was fed via the inlet 12, an electromotive force of about 1 V was generated. It was confirmed with an ammeter 16 that an electric current flowed from the lead 7 to the lead 6, when a switch 15 was on.

The resistance of the solid electrolyte was estimated based on the response of the voltage given when a pulse of an electric current was applied on the cell shown in FIG. 1. The resistance was about 500Ω at 20° C. Since the solid electrolyte had a thickness of 0.2 cm and the electrode area was 0.2 cm$^2$, the specific resistance was 500 Ωcm.

EXAMPLE 2

A solid electrolyte stock solution was prepared in a similar manner as the one described in Example 1. The stock solution was placed in a flat-bottomed glass vessel. Air of a room temperature (about 20° C.) was blown into the vessel to thereby evaporate the moisture, thus solidifying the solution. The obtained solid plate was amorphous and had a molar ratio of C to W of 1:9. When the solid plate was heated, it began to release $CO_2$ at a temperature of about 200° C. and decomposed into $WO_3$. The other characteristics thereof were similar to those of the solid obtained in Example 1. Accordingly, it was apparent that the solid obtained in Example 2 was a heteropolyacid (solid) containing carbon as a heteroatom.

A similar cell as the one produced in Example 1 was produced by the use of the above solid plate. The relationship between the electromotive force generated between the leads 6 and 7 and the hydrogen concentration was examined in a similar manner as the one described in Example 1. As a result of this examination, the concentration dependence represented by the equation 1 was confirmed and the solid was found to be a hydrogen ion-conductive solid electrolyte. The specific resistance of the solid electrolyte was 250 Ωcm.

EXAMPLE 3

The same procedure as the one described in Example 1 was repeated except that molybdenum carbide ($Mo_2C$) was used instead of WC to obtain a solid electrolyte stock solution. The solution was solidified by blowing air to obtain a heteropolyacid having a ratio of C to Mo of about 1:11. A similar cell as the one shown in FIG. 1 was produced by the use of this solid plate. The relationship between the electromotive force generated between the leads 6 and 7 and the hydrogen concentration was examined in a similar manner as the one described in Example 1. As a result of this examination, the concentration dependence represented by the equation 1 was observed. The specific resistance of the solid electrolyte was 300Ω (at 20° C.).

EXAMPLE 4

The same procedure as the one described in Example 1 was repeated except that a mixture comprising WC and $MO_2C$ at a molar ratio of 18:1 instead of WC was reacted with $H_2O_2$ to obtain a solid electrolyte stock solution. The stock solution was placed in a flat-bottomed glass vessel and solidified by blowing air. The obtained solid was a heteropolyacid having a molar ratio of C to metal (W+Mo) of about 1:9. A similar cell as the one shown in FIG. 1 was produced by the use of the above plate. The relationship between the electromotive force generated between the leads 6 and 7 and the hydrogen concentration was examined to observe the concentration dependence represented by the equation 1, thus confirming that the obtained heteropolyacid containing carbon, tungsten and molybdenum was also a hydrogen ion-conductive solid electrolyte. The solid electrolyte had a specific resistance of about 300Ω (at 20° C.).

INDUSTRIAL APPLICABILITY

As described above, the solid electrolyte of the present invention has excellent effects.

What is claimed is:

1. A solid electrolyte comprising a heteropolyacid, the principal component of which is a heteropolytungstic acid and/or heteropolymolybdic acid containing carbon as a heteroatom.

2. A solid electrolyte as set forth in claim 1, wherein the heteropolyacid is a heteropolytungstic acid.

3. A solid electrolyte as set forth in claim 1, wherein the heteropolyacid is one which comprises a heteropolyanion represented by the general formula, $C_xM_yO_z{}^{m-}$ (wherein M is at least one element selected from the group consisting of W and Mo and the ratio of x to y is between 1:12 and 4:12) and a hydrated proton represented by the formula $H(m' H_2O)^+$.

* * * * *